US009766205B2

(12) United States Patent
Staal et al.

(10) Patent No.: US 9,766,205 B2
(45) Date of Patent: Sep. 19, 2017

(54) APPARATUS FOR THE MEASUREMENT OF A CONCENTRATION OF A CHARGED SPECIES IN A SAMPLE

(71) Applicant: Medimate Holding B.V., Enschede (NL)

(72) Inventors: Steven S. Staal, Enschede (NL); Jan Floris, Enschede (NL); Stefan O. Lenk, Enschede (NL)

(73) Assignee: CE-MATE B.V., Enschede (NL)

( * ) Notice: Subject to any disclaimer, the term of this patent is extended or adjusted under 35 U.S.C. 154(b) by 459 days.

(21) Appl. No.: 14/281,451

(22) Filed: May 19, 2014

(65) Prior Publication Data

US 2014/0251812 A1 Sep. 11, 2014

Related U.S. Application Data

(62) Division of application No. 13/202,022, filed as application No. PCT/EP2009/051874 on Feb. 17, 2009, now Pat. No. 8,728,292.

(51) Int. Cl.
*G01N 27/447* (2006.01)
(52) U.S. Cl.
CPC . *G01N 27/44756* (2013.01); *G01N 27/44704* (2013.01); *G01N 27/44791* (2013.01)
(58) Field of Classification Search
CPC ....... G01N 27/44756; G01N 27/44704; G01N 27/44791
See application file for complete search history.

(56) References Cited

U.S. PATENT DOCUMENTS

| 5,223,114 | A | 6/1993 | Zare et al. |
| 5,580,435 | A | 12/1996 | Kovacs |
| 5,882,496 | A | 3/1999 | Northrup et al. |
| 6,375,817 | B1 * | 4/2002 | Taylor ............... B01L 3/502784 204/453 |
| 7,250,096 | B2 | 7/2007 | Shoji et al. |

(Continued)

FOREIGN PATENT DOCUMENTS

| JP | H04300591 | 10/1992 |
| JP | 6249833 | 9/1994 |
| JP | H980085 | 3/1997 |

(Continued)

OTHER PUBLICATIONS

Korean Notice of Preliminary Rejection issued in KR Application No. 10-2014-7023582 dated Nov. 24, 2014.

(Continued)

*Primary Examiner* — J. Christopher Ball
(74) *Attorney, Agent, or Firm* — Stephen H. Eland; Dann, Dorfman, Herrell & Skillman

(57) ABSTRACT

An apparatus (1) for the measurement of a concentration of a charged species in a sample (10) is disclosed. The sample (10) comprises a plurality of types of charged species and at least one insoluble component. The apparatus (1) comprises a first circuit with a voltage control device (54) connectable to two first electrodes (30, 30') arranged along a channel (12) holding the sample (10) and a second circuit with a conductivity detection device (55) connectable to two second electrodes (5, 5') arranged in the channel (12). The first circuit and the second circuit are dc and ac electrically isolated from each other.

7 Claims, 8 Drawing Sheets

(56) References Cited

U.S. PATENT DOCUMENTS

2004/0018638 A1    1/2004    Shoji et al.
2005/0150766 A1    7/2005    Manz et al.

FOREIGN PATENT DOCUMENTS

| JP | 11023521 | | 1/1999 |
|----|----------|---|--------|
| JP | 2004093573 | | 3/2004 |
| JP | 2005-517159 | | 6/2005 |
| JP | 2006145437 | | 6/2006 |
| JP | 2006-226752 A1 * | 8/2006 |
| WO | 96/33405 | | 10/1996 |
| WO | 2008/061542 | | 5/2008 |

OTHER PUBLICATIONS

Vrouwe et al., Direct Measurement of Lithium in Whole Blood Using Micorchip Capilary Electrophoresis With Integrated Conductivity Detection (XP-002447049), Electrophoresis, 2004, 25, pp. 1660-1667.

Vrouwe et al., Microship Analysis of Lithium in Blood Using Moving Boundary Electrphoresis and Zone Electrophoresis, Electrophoresis, 2005, 26, pp. 3032-3042.

Schlautmann, et al. "Power-Blasting Technology as an Alternative Tool for Microfabrication of Capillary Electrophoresis Chips with Integrated Conductivity Sensors" Journal of Micromechanics and Microengineering, vol. 11, 2011, pp. 386-389.

Martin et al, "In-Channel Electrochemical Detection for Microchip Capillary Electrophoresis using an Electrically Isolated Potentiostat" Analytical Chemistry, vol. 74, No. 5, Mar. 2002, pp. 1136-1143.

Official Action issued in Japanese Application No. 2011-549443 dated Oct. 8, 2013.

Official Action issued in Japanese Application No. 2011-549443 dated Mar. 5, 2013.

International Preliminary Report & Written Opinion issued in International Application No. PCT/EP09/51874 dated Aug. 23, 2011.

Vrouwe et al, "Microchip Capillary Electrophoresis for Point-of-Care Analysis of Lithium", Clinical Chemistry, 53:1, (2007) pp. 117-123.

* cited by examiner

APPARATUS FOR THE MEASUREMENT OF A CONCENTRATION OF A CHARGED SPECIES IN A SAMPLE

CROSS-REFERENCE TO OTHER APPLICATIONS

This application is a divisional application of U.S. application Ser. No. 13/202,022 filed Oct. 11, 2011, which is a U.S. National Stage application of International Patent Application No. PCT/EP09/51874 filed Feb. 17, 2009. Each of the foregoing applications are herby incorporated herein by reference.

FIELD OF THE INVENTION

The invention relates to an apparatus and method for sensing of charged species in biological, chemical, industrial or environmental samples. In particular, the invention relates to a method and an apparatus for measuring charged species concentrations, in particular ion concentrations, for example lithium ion concentrations, in samples, such as blood.

BACKGROUND AND RELATED ART

Inorganic ions are an essential requirement for life and are found in large amounts in drinking water, blood and every cell of an organism as well as in the environment. For example, the concentration of many ions i.e. sodium, potassium, magnesium, and calcium inside and outside of cells is essential for any living organism. Consequently, the ion concentration in the blood and blood cells of animals and human beings also is of high importance for a large variety of body functions.

Normally lithium is a trace element present in blood plasma. Lithium is also used as a drug to treat bipolar mood disorder. It is estimated that worldwide over one million people take lithium on a daily basis. A disadvantage in the use of lithium is the very low therapeutic index, i.e. the ratio between the toxic concentration and the therapeutic concentration. Most patients respond well to a blood plasma concentration of 0.4-1.2 mmol/L lithium while toxic effects can occur at a lithium concentration of above 1.6 mmol/L. A prolonged high blood lithium level can even result in permanent damage to the nervous system and even death. Monitoring of the lithium concentration during treatment is therefore essential, with regular checks every couple of months to keep the lithium level at desired level.

To avoid extensive operator handling, ion-selective electrodes (ISEs) are routinely used for measurements of blood parameters in an automated fashion. These ISEs are fast and offer a large dynamic range. However, their response is logarithmic and the required high selectivity for lithium can be a problem. Additionally, in case of lithium intoxication a fast procedure for blood analysis is required. Currently, a venous blood sample must be withdrawn from the patient by specially trained personnel and transported to the central laboratory and the blood cells need to be removed before the measurement is made. This procedure can take up to 45 minutes. To minimize sample throughput time and enable measurements on location, miniaturized devices employing ion-sensitive field-effect transistors are available to determine the concentration of potassium and sodium in whole blood even as a hand-held analyzer. However, such analyzers are not used for lithium determination, because of the high background concentration of other charged species, in particular sodium ions, compared to the much smaller concentration of lithium ions.

The direct measurement of lithium in whole blood and the determination of inorganic cations in blood plasma have been described and demonstrated by E. Vrouwe et al. in Electrophoresis 2004, 25, 1660-1667 and in Electrophoresis 2005, 26, 3032-3042. Using microchip capillary electrophoresis (CE) with defined sample loading and applying the principles of column coupling, a concentration of alkali metals was determined in a drop of whole blood. The whole blood collected from a finger stick was transferred onto a microchip without extraction or removal of components of the whole blood. The lithium concentration can be determined in the blood plasma from a patient on lithium therapy without sample pre-treatment. Using the microchip with conductivity detection, a detection limit of 0.1 mmol/L has been obtained for lithium in a 140-mmol/L sodium matrix.

Other prior art documents disclosing several types of the microchips for the measurement of the concentration of ions in the blood sample are known in the art. For example, US Patent Application US 2005-0150766 (Manz) discloses a capillary electrophoresis microchip.

U.S. Pat. No. 5,882,496 (Northrup et al) discloses a method for fabrication and use of porous silicon structures to increase a surface area of one of electrophoresis devices.

U.S. Pat. No. 7,250,096 (Shoji et al, assigned to Hitachi High-Technologies Corp) teaches a method and apparatus for measuring a current-carrying path during electrophoresis to detect the state of the current-carrying path.

One of the issues in the prior art is a formation of gas bubbles in the electrolyte at the electrodes (as noted in U.S. Pat. No. 7,250,096) and/or undesired redox (reduction-oxidation) reaction due to electrolysis at electrodes in a microchannel of the apparatus. This occurs because the charge transport through the apparatus is carried by electrons in an electric path and ions in a chemical path. The charge is exchanged between electrodes and ions at the electrodes.

The electrolyte in the microchannel has a specific gas capacity. The maximum amount of the specific gas capacity is termed the gas limit. The gas bubbles are formed when the gas limit is reached locally within the microchannel. The formation of gas bubbles directly influences the measurements.

The ions and other uncharged molecules undergo changes due to redox reactions and changing concentrations at the electrodes. The gas bubbles are formed due to the formation of non-charged molecules which exceed the gas limit and form gas bubbles. These gas bubbles are confined within the microchannel of the device and as a result can distort the measurements.

The formation of the gas bubbles can be avoided as is explained in prior art if there is a single electrical circuit for capillary electrophoresis measurement or a single electrical circuit for in contact conductivity detection and voltage and or current is controlled adequately. However, if there are two electrical circuits for the measurement method combined, then the electrical interference of both electrical circuits adds complications.

Prior art methods of resolving this problem for single electrical circuits include the use of alternating current between the electrodes, by limiting of the electrical current, by controlling the type of redox reaction and by reducing the voltage below the redox potential. Limiting the current can for instance be realized by using a current source, small channel geometries and low concentrations of the electrolyte in a channel. It is also possible to use a low concentration of background electrolyte in a channel. Furthermore the design of the electrodes can play a role. Electrodes with large surface area are less susceptible to the formation of gas bubbles since the charge concentration changes are spread over a larger area.

SUMMARY OF THE INVENTION

The invention provides an apparatus for the measurement of a concentration of a charged species in a sample. The sample comprises a plurality of types of charged species and at least one insoluble component. The apparatus comprises a first circuit with a voltage control device connectable to at least two first electrodes arranged along a channel holding the sample and a second circuit with a conductivity detection device connectable to at least two second electrodes arranged in the channel, wherein the first circuit and the second circuit are electrically isolated from each other The electrical isolation means that the two electrical circuits do not interfere with each other and therefore the measurements are accurate.

DESCRIPTION OF THE DRAWINGS

The invention may be better understood with respect to the figures and the detailed description of preferred embodiments, which is illustrative only and not limiting to the invention and wherein.

DETAILED DESCRIPTION OF THE INVENTION

The invention will now be described with respect to the figures and examples. It will be noted that features from one aspect of the invention may be combined with features from another aspect of the invention.

Figure 1A:
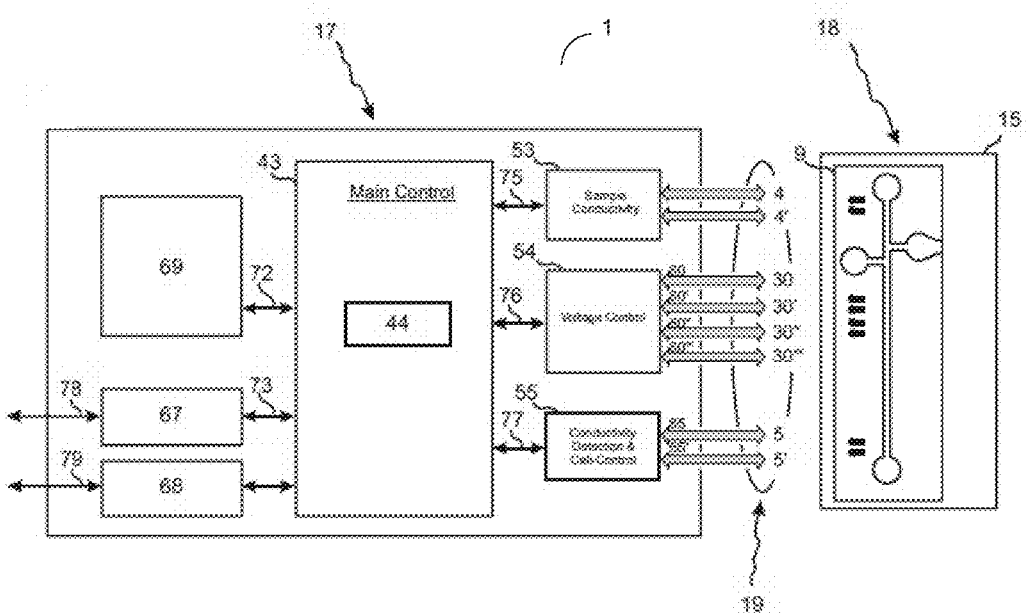
FIG. 1a shows main components of an apparatus according to one aspect of the invention.
Figure 1B:
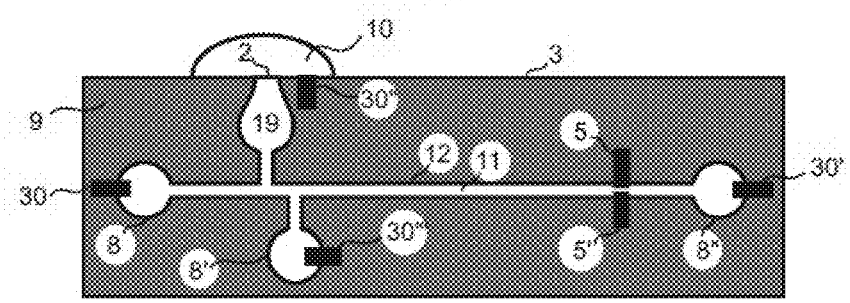
FIGS. 1b and 1c show arrangement of electrodes about a microchannel.
Figure 1C:
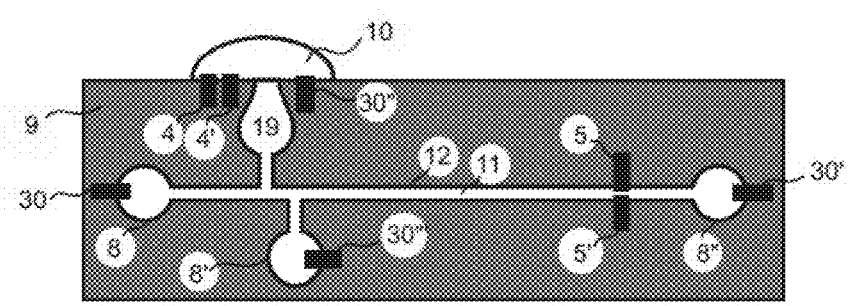

FIGS. 1a to 1c show the components of a measurement system 1 according to one aspect of the invention.

The measurement system 1 comprises a measuring device 17 which measures and processes electrical signals from a sensor 18. The sensor 18 measures a concentration of charges species in a liquid sample 10 (shown in FIGS. 1b and 1c) and is disclosed more fully in the co-pending international patent application no WO 2008/061542, the teachings of this patent application are fully incorporated herein. The liquid sample 10 is most commonly a blood sample.

The sensor 18 has a chip holder 15 and a sample device 9. The chip holder 15 is disclosed more fully in international patent application no. PCT/EP2007/004468, the teachings of which are fully incorporated herein. The sample device 9 is shown in more detail in FIGS. 1b and 1c and will be explained in more detail in conjunction with these figures.

The measuring device 17 has a sample conductivity measurement device 53, a voltage control and current sense device 54 and a conductivity detection and cell control device 55. The conductivity measurement device 53 is connected to sample conductivity electrodes 4 and 4' on the sample device 9 through electrical paths. The voltage control and current sense device 54 is connected to reservoir electrodes 30 and 30' and to wall electrodes 30" and 30''' on the sample device 9 through electrical paths 60 to 60''' respectively. Similarly the conductivity detection and cell control device 55 is connected to channel electrodes 5 and 5' on the sample device 9 through electrical paths 65 and 65'.

A main control 43 in the measuring device 17 includes a processor 44 for performing calculations. The main board 43 is connected to the conductivity measurement device 53 through an electrical path 75, to the voltage control and current sense device 54 through an electrical path 76 and to the conductivity detection and cell control device 55 through an electrical path 77.

The measuring device 17 has an LCD display and buttons which are connected to an operating panel 69. The operating panel 69 is connected to the main board 43 through an electrical path 72. The measuring device 17 is supplied with power through a power supply 68 connected to the power supply 79. A serial port 67 is connected to the main board 43 through an electrical path 73 and to an outside connection 78.

The sample device 9 comprises a substrate (not shown) into which a channel 12 is formed, as shown in FIG. 1a and more clearly on FIGS. 1b and 1c. The substrate may be made from glass or plastics material. Any other material allowing for the fabrication of channels 12 may be used. In case of glass as the substrate material, the channel 12 is etched into the substrate 13 between a first reservoir 8, a second reservoir 8' and a third reservoir 8". The side walls of the channel 12 may be coated with a polymer. The channel 12 may be of sub-centimeter dimensions; in particular the channel 12 may be less than 1 cm in width and less than 100 μm in depth. The first reservoir 8, the second reservoir 8' and the third reservoir 8" may be considerably larger in size than the width of the channel 12 (e.g. 100 μm to 1 cm. This can be seen in FIGS. 1b and 1c. Further one or more of the reservoirs may be included in the channel 12.

The channel 12 and the first reservoir 8, the second reservoir 8' and the third reservoir 8" may be filled with an electrolyte 11 prior to use. Typically the volume of the reservoir is around 10 ul.

FIGS. 1b and 1c show a side view of the sample device 9. The sample device in one exemplary embodiment of the invention has a width of 30 mm, a height of 4 mm and a thickness of 1.4 mm. The chip can be made of glass.

It will be seen that the channel 12 as well as the first reservoir 8, the second reservoir 8' and the third reservoir 8" have a number of electrodes. The channel 12 in one exemplary embodiment of the invention is less than 100 um in width, has a depth of less than 100 um and a length of less than 3 cm. It will be further noted that a part 19 is connected between the top surface 3 of the sample device 9 and the channel 12. The sample 10 is placed on the top surface 3 of the sample device 9. The sample 10 is in fluid communication with a part 19 of the channel 12 through an opening 2 in the top surface 3. The opening 2 and the part 19 may have the form of a circle but any form suitable for inserting liquid into the channel 12 may be used.

More than one opening 2 may be made in the top surface 3. This is useful, for example, for allowing the sample 10 to enter into the channel 12 at multiple entry points. This allows for multiple measurements to be made and averages to be taken. One further advantage of more than one opening 2 is to allow convective flow from one opening towards another opening and thus providing an alternative transport mechanism through the opening 2 into the channel 12. One further advantage of more than one opening 2 is to prevent evaporation in channel 12 as is disclosed in international patent application no. PCT/EP2007/004468.

The channel 12 is provided with a number of electrodes which have generally rounded corners to avoid concentration of current. The reservoir electrodes 30, and 30' are provided in the first reservoir 8 and the third reservoir 8'''. The reservoir electrodes 30 and 30' allow a voltage to be placed along the channel 12. The reservoir electrodes 30 and 30' are connected to the voltage control and current sense device 54 through electrical paths as explained above. The reservoir electrodes 30 and 30', as well as the well electrodes as described below, are typically made of Platinum and are flat and thin, typically below 2 mm width and 2 mm length but a height in the order of 100 nm.

The top surface 3 and the other reservoir 8' are provided with the well electrodes 30'' and 30' which allow the placement of a voltage across the channel 12. This is useful for drawing charged ions from the sample 10 through the opening 2 into the cavity 19 and then into the channel 12. The well electrodes 30'' and 30''' are connected to the voltage control and current sense device 54 through the electrical paths as explained above. A typical voltage used is 1200 V and a current would be less than 10 uA.

The channel 12 has two channel electrodes 5 and 5' which are situated substantially opposite to each other and measure the conductivity across the channel 12. The conductivity electrodes 5 and 5' are connected to the conductivity detection and control device 55 through electrical paths as explained above. The two channel electrodes 5 and 5' are around 100 um apart and are also made of platinum. Their width is less than 100 um, for example 40 um, and the two channel electrodes 5 and 5' have mildly rounded corners. The signal applied across the channel is typically AC and in between 100 Hz and 100 kHz with an top-top amplitude between 1 and 10V.

The two channel electrodes 5 and 5' allows the use of an in contact ion detection (abbreviated ICCD) mechanism into the apparatus 1. The ICCD mechanism is a detection method in which the channel electrodes 5 and 5' have a direct electrochemical interface with the fluid in the channel 12.

FIG. 1*c* shows two of the sample conductivity electrodes 4 and 4' on the top surface 3. The sample conductivity electrodes 4 and 4' are covered by the sample 10 and measure the conductivity of charges species in the sample 10 before, during and/or after the charged species are drawn into the part 19 of the microchannel. The sample conductivity electrodes 4 and 4' are connected to the sample conductivity measurement device 53, as explained above. The sample conductivity electrodes 4 and 4' have a generally rounded form which reduces the current density at the tips of the sample conductivity electrodes 4 and 4'.

Figure 2A:
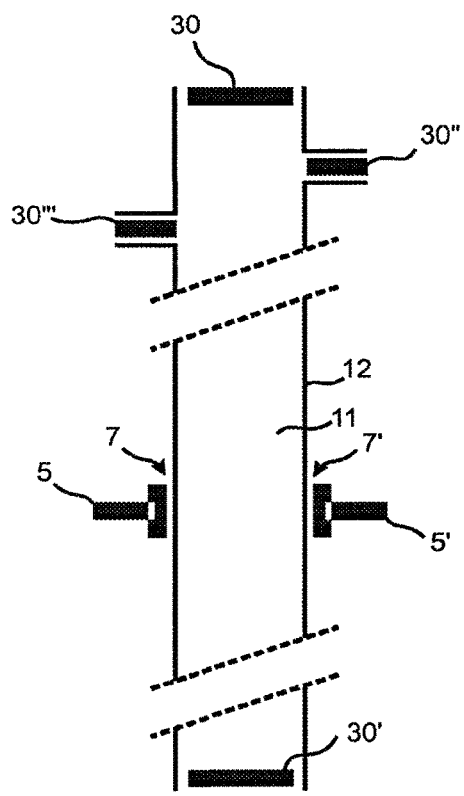
FIGS. 2a and 2b shows further arrangements of the electrodes about the channel.
Figure 2B:
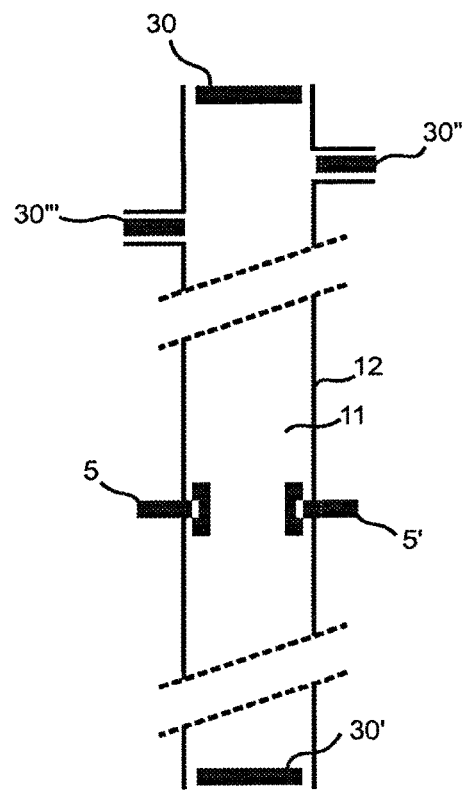

FIGS. 2*a* and 2*b* show the arrangement of the electrodes in the channel 12 in more detail. For simplicity the first reservoir 8, the second reservoir 8' and the third reservoir 8''' are not shown in detail. Only the electrodes 30 to 30''' are shown. In FIG. 2*a* the channel electrodes 5 and 5' are not placed inside of the channel 12 but are outside of the channel walls 7 and 7'. In other words neither of the channel electrodes 5 and 5' are in direct contact with the fluid 11 in the channel 12. In FIG. 2*b* it will be seen that the channel electrodes 5 and 5' penetrate through the side walls 7 and 7' and are in fluid (and direct electrical) contact with the fluid 11 in the channel 12. The aspect of the setup shown in FIG. 2*a* has the advantage that neither of the two channel electrodes 5 and 5' are in direct contact with the fluid 11. As a result it is not possible for gas bubbles to form on the surface of the two channel electrodes 5 and 5'.

In the aspect of the invention shown in FIG. 2*b* it is necessary to ensure that the voltage and or the type of redox reaction and or the electrical current is controlled at the two channel electrodes 5 and 5' in that aspect that the formation of gas stays below the gas limit. In an alternative aspect of the invention, an alternating current can be passed across the two channel electrodes 5 and 5'.

Figure 3A:
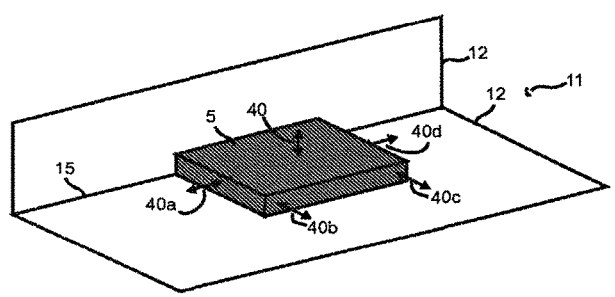
FIGS. 3a and 3b illustrate possible current paths at one electrode or in between electrodes.
Figure 3B:
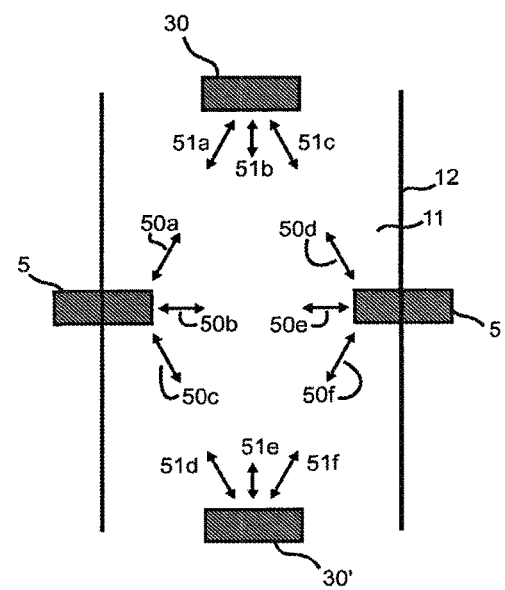

FIGS. 3*a* and 3*b* show the current paths on the various electrodes 30 and 30', the current paths on the electrodes 30'' and 30''' are not shown for clarity but are also present. FIG. 3*a* shows one exemplary channel electrode 5 (or 5') within the channel 12 (i.e. the aspect of the invention shown in FIG. 2*b*). The current paths 40*a* and 40*d* are present along the channel 12 towards the reservoir electrodes 30 and 30'. The current paths 40, 40*c* and 40*b* act across the channel 12.

FIG. 3*b* shows the current paths acting on the reservoir electrodes 30 and 30' as well as on the channel electrodes 5 and 5'. It will be noted that the reservoir electrode 30 has a current path 51*a* in the direction of the channel electrode 5 and a current path 51*c* in the direction of the channel electrode 5' as well as a current path 51*b* in the direction of the other reservoir electrode 30'. Similarly the reservoir electrode 30' has a current path 51*d* in the direction of the channel electrode 5 and a current path 51*f* in the direction of the channel electrode 5' as well as a current path 51*e* in the direction of the other reservoir electrode 30.

The channel electrode 5 has a current path 50*a* in the direction of the reservoir electrode 30 and a current path 50*c* in the direction of the reservoir electrode 30' as well as a current path 50*b* in the direction of the channel electrode 5'. The channel electrode 5' has a current path 50*d* in the direction of the reservoir electrode 30 and a current path 50*f* in the direction of the reservoir electrode 30' as well as a current path 50*e* in the direction of the channel electrode 5.

FIGS. 3*a* and 3*b* illustrate one of the problems in combining capillary electrophoresis methods for separating the ions with in contact conductivity detection. Not only are the electrical potentials between the channel electrodes 5 and 5' and between the reservoir electrodes 30 and 30' relevant, but it is also necessary to consider "cross electrode" or "cross mechanism" current paths given by the reference numerals 50*a*, 50*c*, 50*d*, 50*f* and 51*a*, 51*c*, 51*d*, 51*f*. There needs to be isolation between the circuit including the channel electrodes 5 and 5' and the circuit formed from the circuit including the reservoir electrodes 30 and 30'. This issue is more acute in small scale apparatus, such as that of the invention.

This can be done by electrically ensuring that there is no or reduced common dc or ac connection through the electronics. This is illustrated in FIGS. 4*a* and 4*b* which show in the top halves as an electrical isolator 80 near the circuit for voltage control 54 and in the bottom halves as an electrical isolator 80' near the circuit for the conductivity detection 55.

The reservoir electrodes 30 to 30''' are connected by the electrical paths 60 to 60''' to the voltage control and current sense device 54. The well electrodes 5 and 5' are connected to the conductivity detection and cell control device 55 through the electrical paths 65 and 65'.

Figure 4A:
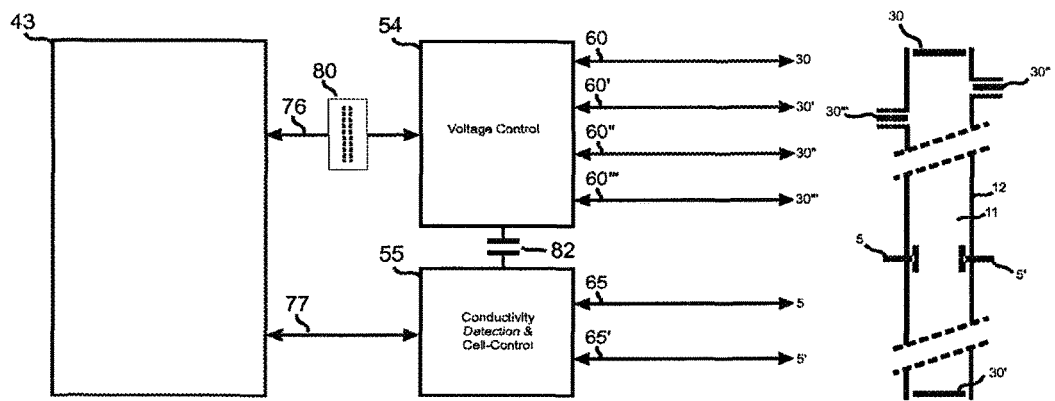
FIGS. 4a and 4b show the connection of the components of the apparatus to the electrodes about the microchannel.
Figure 4B:
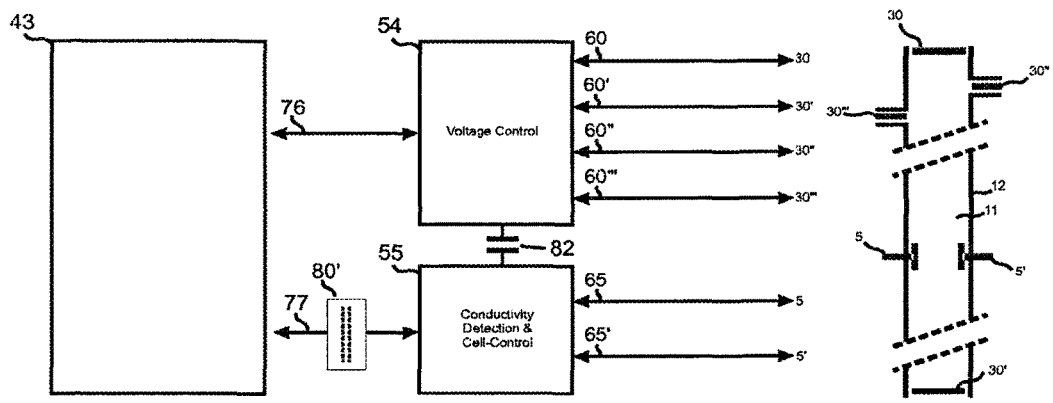

In FIG. 4a the voltage control and current sense device 54 is connected to the main board through an electrical isolator 80. In FIG. 4b the conductivity detection and cell control device 55 is connected to the main board 43 through an isolator 80'. The purpose of the electrical isolators 80 and 80' is to isolate the various electrodes from each other. The electrical isolators 80 and 80' are shown in an exemplary position in FIGS. 4a and 4b, but it will be noted that they can be placed in other positions. It will also be note that more than one electrical isolator 80 and 80' can be included. In general it can be stated that an electrical isolator 82 with a low capacitance has to be realized between the voltage control circuit 54 and the conductivity detection circuit 55 in combination with the electrodes 30 to 30''' and 5 to 5''.

Figure 5A:
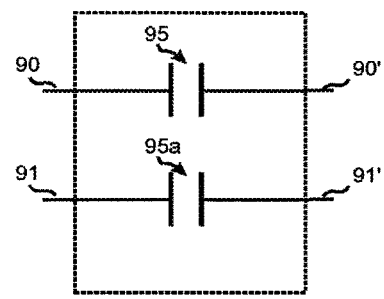
FIGS. 5a to 5d show different arrangements of isolation components.
Figure 5B:
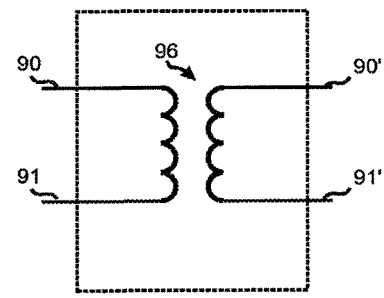
Figure 5C:
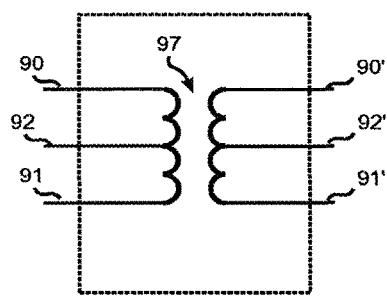
Figure 5D:
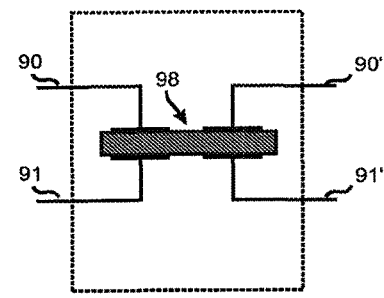

The electrical isolators 80 and 80' can have various configurations as shown in FIGS. 5a to 5d. In FIG. 5a the input of each of the two electrical paths 90 and 91 is isolated from the output of the two electrical paths 90' and 91' by a capacitor 95 and 95a. Similarly in FIG. 5b the input of each of the two electrical paths 90 and 91 is isolated from the output of the two electrical paths 90' and 91' by an inductor 96. In FIG. 5c an inductor 97 has a central tap 92, 92'. In FIG. 5d a piezo element 98 is caused to isolate the input of the electrical paths 90 and 91 from the output of the electrical paths 90' and 91'.

The isolators 80 and 81 have the effect of substantially reducing the dc current between the capillary electrophoresis circuit and the ICCD circuit. One further problem that can arise is the presence of an ac current between the capillary electrophoresis circuit and the ICCD circuit. This can be reduced by using the electrical isolators 80 and 80' as well.

It will be noted that the reduction in the capacitance 82 is advantageous for the apparatus in order to reduce dc and ac effects. It is thought that a capacitance of less than 100 pF, for example, 20 pF is optimal in order to be able to accurately measure the ions in the channel 12.

Figure 6:
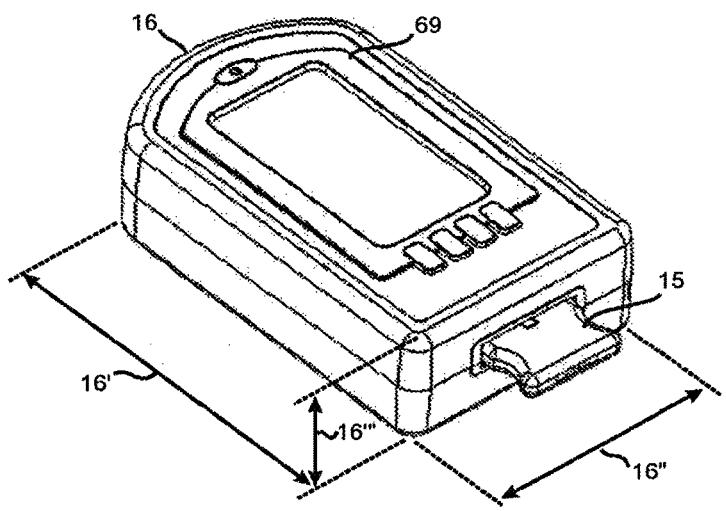
FIG. 6 shows an example of a measuring device.

FIG. 6 shows an example of the measuring device with a display 69. The width 16'' is generally less than 50 cm and in one exemplary embodiment is 10 cm. The height 16''' is less than 10 cm and in one exemplary embodiment is 5 cm. The depth 16' is less than 50 cm and in one exemplary embodiment is 20 cm.

Figure 7:
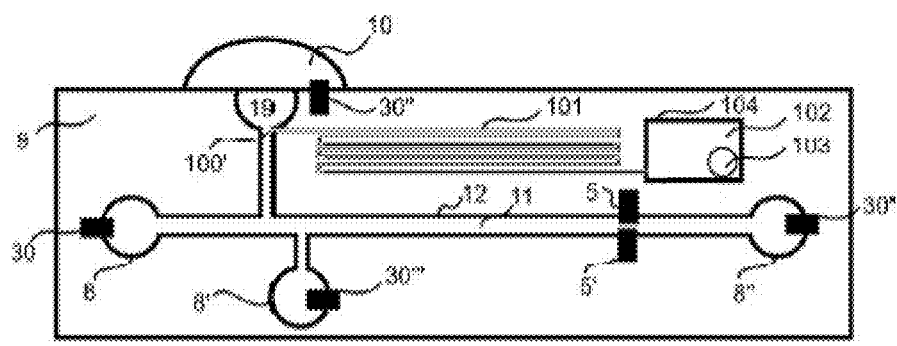
FIG. 7 shows an example of an apparatus with an expansion chamber

A further embodiment of the invention is shown in FIG. 7 in which an expansion chamber 104 is connected through an opening 100' and interconnection 101 to the part 19 of the microchannel 19 at entry 100'. It will be noted that the interconnection 101 has a cross section which is smaller than the cross section of the channel 12. It will be further noted that the interconnection is long and curves back and forwards in order to use the least amount of space. This is useful in order to increase the aerodynamic resistance of the interconnection 101 to the expansion chamber 104 with respect to the channel 12 and the other reservoirs.

The expansion chamber 104 is filled with a fluid 102, such as the electrolyte 11. A gas bubble 103 is present inside of the fluid 102. The gas bubble 103 is preferably made of a gas, such as an inert gas, e.g. helium, argon.

The expansion chamber 104 with the gas bubble 103 allows the fluid in the microchannel 12 to expand and shrink due to temperature differences without destroying the chip. Temperature differences of a few degrees but also for instance 50 degrees can be dealt with in this manner. This is necessary to enable efficient operation of the apparatus. If, for example, the fluid in the microchannel 12 expanded so much that the fluid leaked out of the chip, then on cooling the microchannel 12 would no longer be completely filled with the fluid which would lead to a change in measurements. It will be noted that the expansion chamber 104 has a substantial volume in comparison with the volume of reservoirs 8 to 8'' and channel 12 in that manner that the gas bubble 103 created is capable of resisting the temperature differences and preventing leakage.

The gas bubble 103 is generated by evacuating air from the sample device 9 and then adding the inert gas to the microchannel 12 that seeps into the expansion chamber 104. The sample device 9 is then evacuated again and the fluid is placed at the sample device 9. The sample device 9 is then brought to atmospheric pressure and the fluid enters the sample device. Due to the residual gas in the expansion chamber 104a gas bubble 103. In another method, the gas bubble 103 can be formed by electrolysis of water. This requires, of course, electrodes to be present in the expansion chamber 104. The amount of evacuation of the expansion chamber 104 governs the formation of the gas bubble 102. The higher aerodynamic resistance of the interconnection 101 means, for instance, that gas leaks out more slowly from the expansion chamber 104 than from the channel 12. This means that it is possible to substantially evacuate the channel 12 but still have some gas left in the expansion chamber 104. On filling of the sample device with the fluid, the remaining gas left in the expansion chamber 104 forms the air bubble.

It will be noted that the use of the expansion chamber 104 is substantially greater than in the described sample device 9. For example, the expansion chamber 104 can be used in other microfluidic devices to compensate for the expansion/shrinkage of fluid incorporated into the microchannels of the microfluidic devices.

Figure 8:
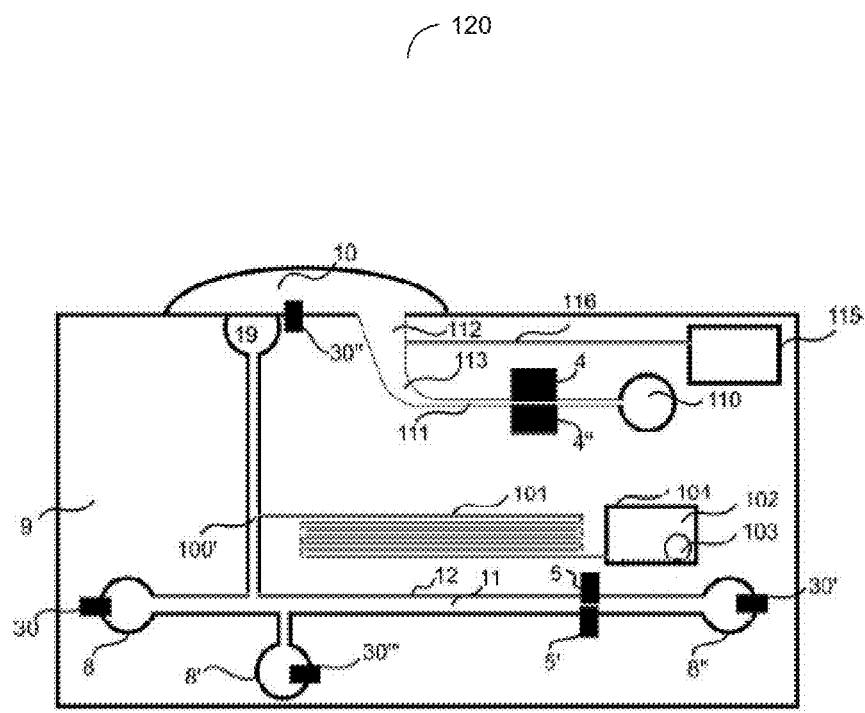
FIG. 8 shows an example of an apparatus with an sample conductivity measurement included In the figures same reference numerals describe the same or similar objects.

The sample conductivity can also be measured with another sample system 120. In FIG. 8a typical aspect is shown of this sample system 120. In this aspect of the invention a sample entry 112 is implemented connected by a channel smoothening 113 and a sample channel 111 to a sample reservoir 110. The sample reservoir 110 is typically open to air. For this aspect of the invention there is typically no direct connection to the channel system 12.

The sample system 120 is typically dry prior to use. The filling of the sample system 120 after applying a sample 10 on the surface top is achieved through the sample entry 112 and the channel smoothening 113. This prevents the formation of gas bubbles and to allow proper filling of the sample channel 111 around the electrodes 4 and 4'. The filling is achieved by for instance hydrodynamic pressure made possible by an opening to air in the sample reservoir 110.

Care has to be taken for the correct filling of the sample system 120 due to the combined usage with the filled channel system 12. The sample system 120 is during production filled with the electrolyte 11. The electrolyte 11 has to be removed from the sample system 120. This removal is done through the open sample reservoir 110 that is used to dry the electrolyte 11 to air. In this aspect care has to be taken that no sedimentation is created in the sample system 120 during the evaporation of the electrolyte 11 because this will effect the later sample filling. An evaporation chamber 115 is implemented connected by a evaporation channel 116 to the sample system 120. The entry of the evaporation channel 116 is placed close to the sample entry 112. The evaporation chamber 115 is typically a closed chamber. Due to the evaporation chamber 115 and evaporation channel 116 the evaporation of the electrolyte 11 will terminate in the evaporation chamber 115 and therefore the sedimentation of species will take place inside the evaporation chamber instead of inside the sample channel system 120.

It will be noted that the use of the sampling channel system 120, evaporation channel 116 and evaporation chamber 115 is substantially more greatly application than use in the sample device 9 disclosed in FIGS. 1*a*-1*c*. For example, the sampling chamber 120 with the evaporation channel 116 and the evaporation chamber 115 can be used in other micro fluidic devices to determine for instance the sample conductivity and plasma conductivity. An example is the measurement of the haemoglobin level.

The invention has been described with respect to several embodiments. It will, however, be clear to those skilled in the art that the invention is not limited thereto. Rather the cope of the invention is to be interpreted in conjunction with the following claims.

The invention claimed is:

1. Method of fabricating an apparatus, comprising the steps of
    interconnecting a microfluidic channel system with an expansion chamber, for fluidly connecting the expansion chamber with the microfluidic channel system,
    partially evacuating the microfluidic channel system and the expansion chamber,
    covering the microfluidic channel system with a fluid,
    increasing the pressure at the microfluidic channel system and the expansion chamber,
    filling at least partially the microfluidic channel system with the fluid,
    filling at least partially the expansion chamber with the fluid,
    forming a gas bubble in the fluid present in the expansion chamber,
    closing the channel system, thereby obtaining a closed microfluidic channel system.

2. Method according to claim 1, comprising the step of adding an inert gas to the microfluidic channel, the inert gas seeping into the expansion chamber.

3. Method according to claim 1, comprising the step of partially evacuating an inert gas from a sample device.

4. Method according to claim 1, wherein the gas is air.

5. Method according to claim 1, wherein the step of forming the gas bubble comprises a step of water electrolysis.

6. An apparatus comprising:
    an open and unfilled microfluidic channel;
    at least two electrodes placed at the open and unfilled microfluidic channel;
    a sample opening;
    an open sample reservoir;
    a closed evaporation chamber.

7. The apparatus according to claim 6, wherein a channel smoothening is located between the sample opening and the open and unfilled microfluidic channel.

* * * * *